United States Patent
Gaylord et al.

(10) Patent No.: US 8,246,560 B2
(45) Date of Patent: Aug. 21, 2012

(54) HAND BRACE FOR IMMOBILIZING AND ADJUSTABLY POSITIONING ONE OR MORE DIGITS

(75) Inventors: Eric Lee Gaylord, Matthews, NC (US); Robert Scott Gaylord, Matthews, NC (US)

(73) Assignee: Medical Specialties, Inc., Charlotte, NC (US)

( * ) Notice: Subject to any disclaimer, the term of this patent is extended or adjusted under 35 U.S.C. 154(b) by 410 days.

(21) Appl. No.: 12/542,959

(22) Filed: Aug. 18, 2009

(65) Prior Publication Data
US 2011/0046530 A1   Feb. 24, 2011

(51) Int. Cl.
*A61F 5/00*   (2006.01)
(52) U.S. Cl. .......................................................... 602/21
(58) Field of Classification Search .................. 602/5, 6, 602/12, 20, 21, 22; 128/879, 880; 2/16, 2/20, 21, 163, 161.1, 161.6; D24/190
See application file for complete search history.

(56) References Cited

U.S. PATENT DOCUMENTS

| | | | |
|---|---|---|---|
| 4,407,499 A | 10/1983 | Newton | |
| 4,716,892 A * | 1/1988 | Brunswick | 602/21 |
| 5,058,576 A * | 10/1991 | Grim et al. | 602/21 |
| 5,160,314 A | 11/1992 | Peters | |
| 5,415,624 A | 5/1995 | Williams | |
| 5,649,900 A | 7/1997 | Kline | |
| 5,713,837 A * | 2/1998 | Grim et al. | 602/6 |
| 5,728,059 A | 3/1998 | Wiesemann et al. | |
| 5,772,620 A | 6/1998 | Szlema et al. | |
| 5,987,641 A * | 11/1999 | Walker | 2/16 |
| 6,102,880 A | 8/2000 | Nelson et al. | |
| 6,190,344 B1 | 2/2001 | Bobroff | |
| 6,261,253 B1 | 7/2001 | Katzin | |
| 6,561,994 B1 | 5/2003 | Mills et al. | |
| 6,618,624 B2 * | 9/2003 | Elias | 607/48 |
| 6,730,053 B1 | 5/2004 | Bodenschatz et al. | |
| 6,913,582 B2 | 7/2005 | Chen et al. | |
| 6,953,441 B2 | 10/2005 | Goumas | |
| 7,033,331 B1 | 4/2006 | Hely | |
| 7,276,039 B2 * | 10/2007 | Garelick et al. | 602/21 |
| 7,278,980 B1 * | 10/2007 | Garelick et al. | 602/21 |
| 7,318,812 B2 | 1/2008 | Taylor et al. | |
| 7,364,556 B2 | 4/2008 | Weaver, II | |
| 7,402,149 B1 * | 7/2008 | Garelick et al. | 602/21 |
| 7,442,177 B1 * | 10/2008 | Garelick et al. | 602/21 |
| 7,455,650 B1 * | 11/2008 | Garelick et al. | 602/21 |
| 7,537,577 B2 | 5/2009 | Phelan et al. | |
| 2002/0002348 A1 | 1/2002 | Wiggins et al. | |
| 2004/0186403 A1 | 9/2004 | Bodenschatz et al. | |
| 2005/0101898 A1 | 5/2005 | Cohen | |
| 2006/0149180 A1 | 7/2006 | Phelen | |
| 2009/0093744 A1 * | 4/2009 | MacArthur | 602/22 |

* cited by examiner

*Primary Examiner* — Patricia Bianco
*Assistant Examiner* — Raymond E Harris
(74) *Attorney, Agent, or Firm* — Summa, Additon & Ashe, P.A.

(57) ABSTRACT

The invention relates to a hand brace for immobilizing and adjustably positioning one or more digits of the hand, and more specifically, to a brace having a flexible sheet member for application to a wrist and hand, at least one adjustable stabilizing member extending the length of the sheet member that is sufficiently rigid to maintain joints at a desired angle of flexion, a semi-rigid member positioned against the flexible sheet member for protecting and supporting joints of the hand and defining an opening for relieving pressure on a joint, and straps for adjustably securing the invention to the hand. Advantageously the invention immobilizes the hand such that the fourth and fifth metacarpophalangeal joints of the hand are positioned at a desired angle of flexion and fourth and fifth interphalangeal joints of the hand are positioned at a desired angle of extension.

23 Claims, 4 Drawing Sheets

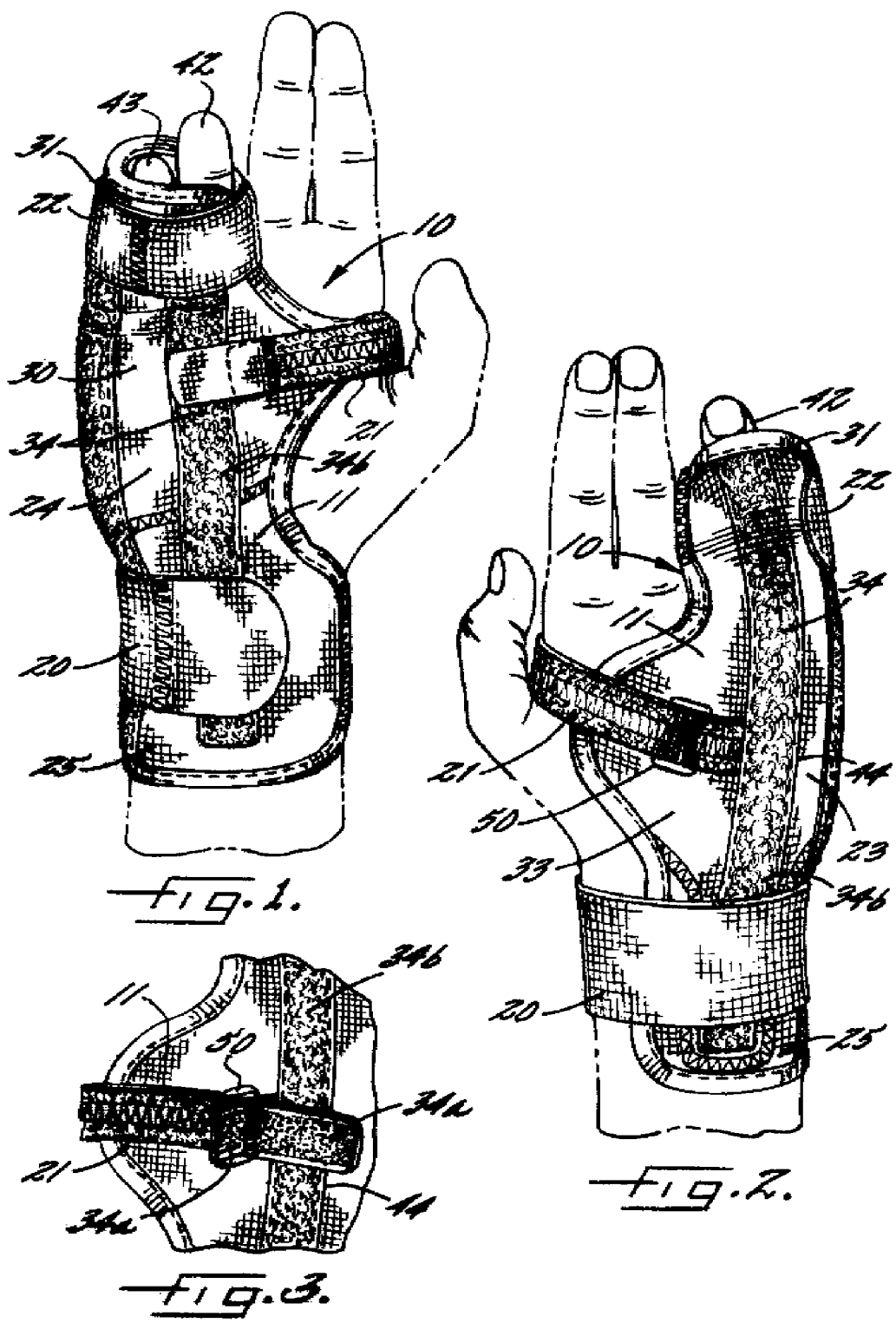

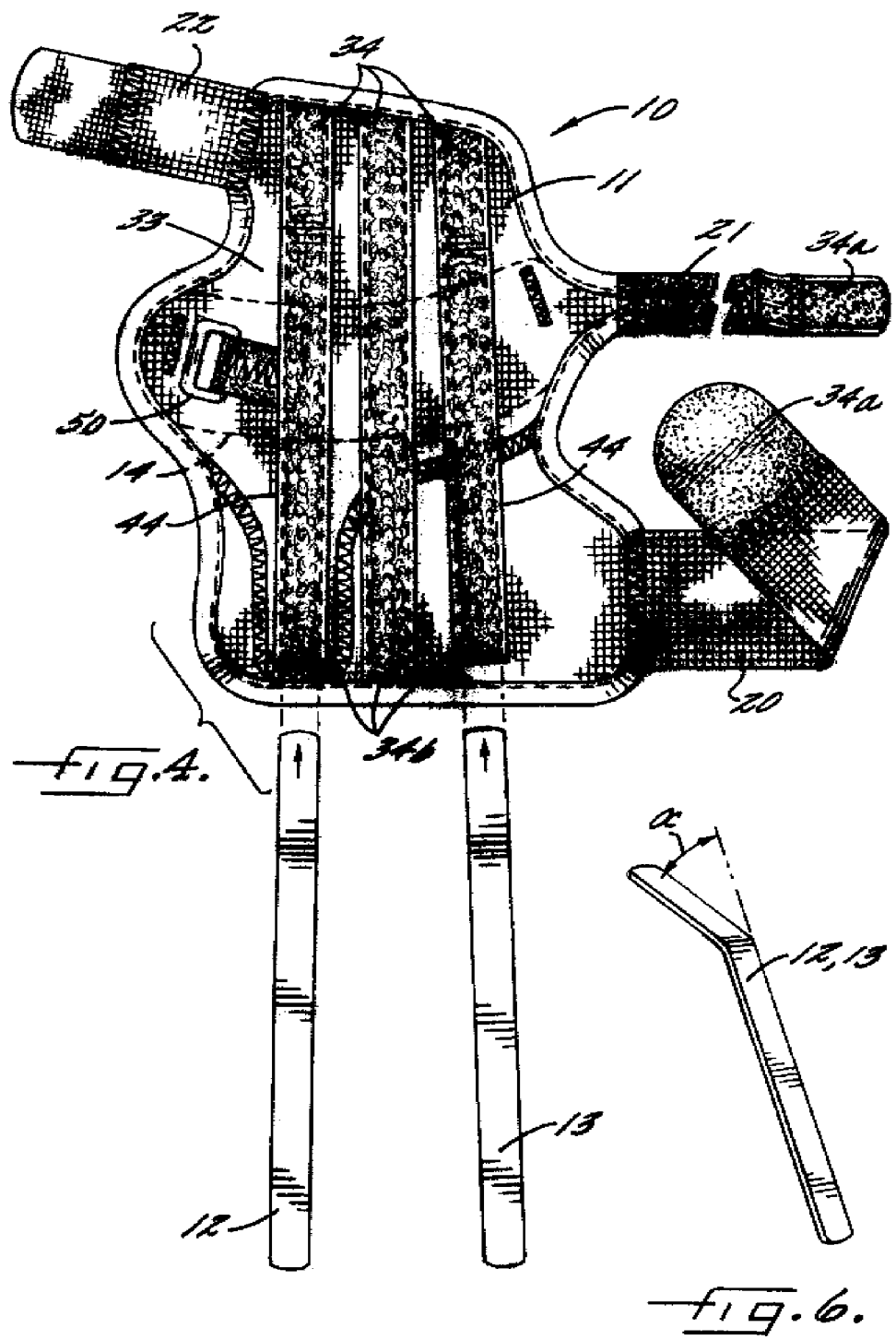

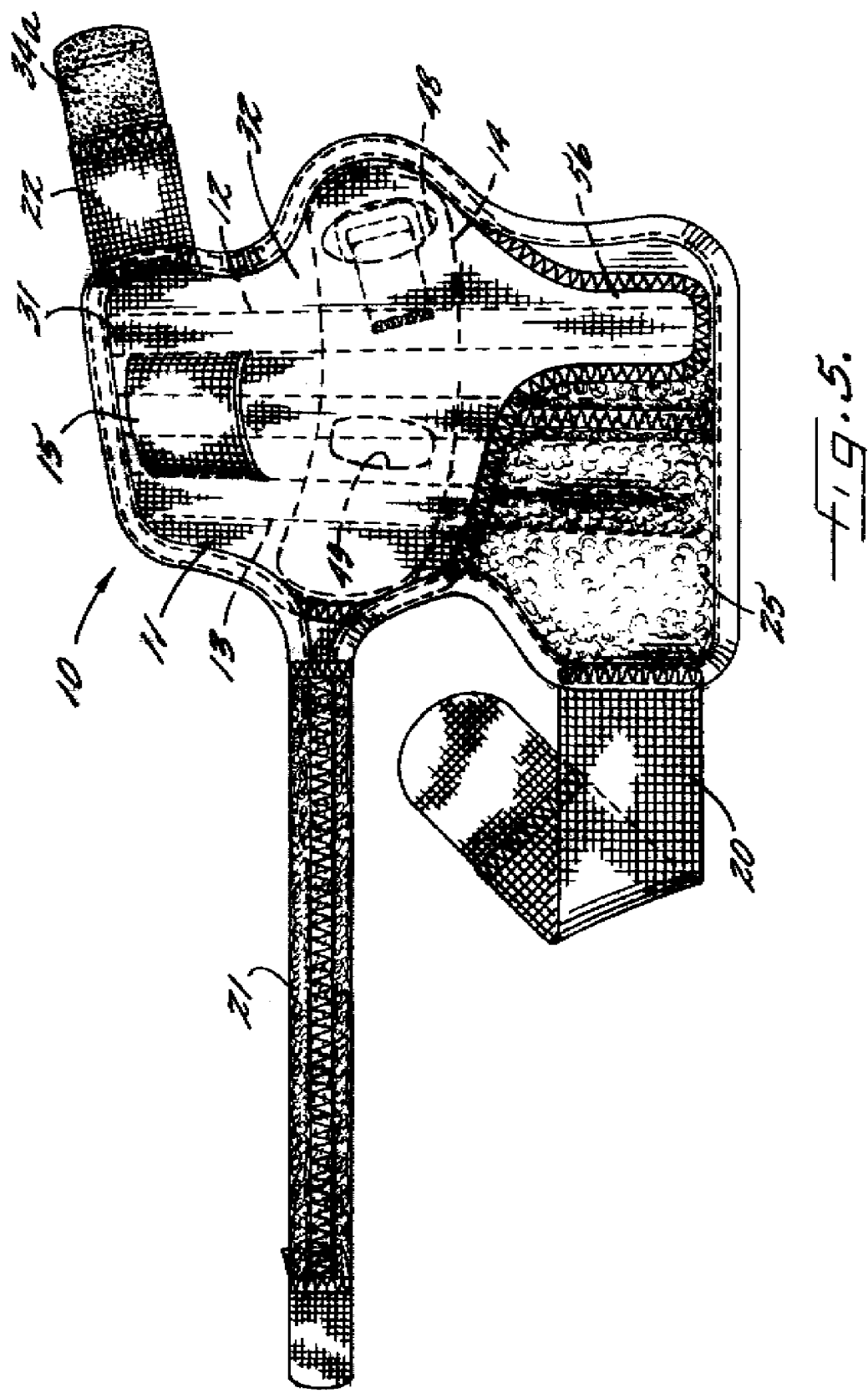

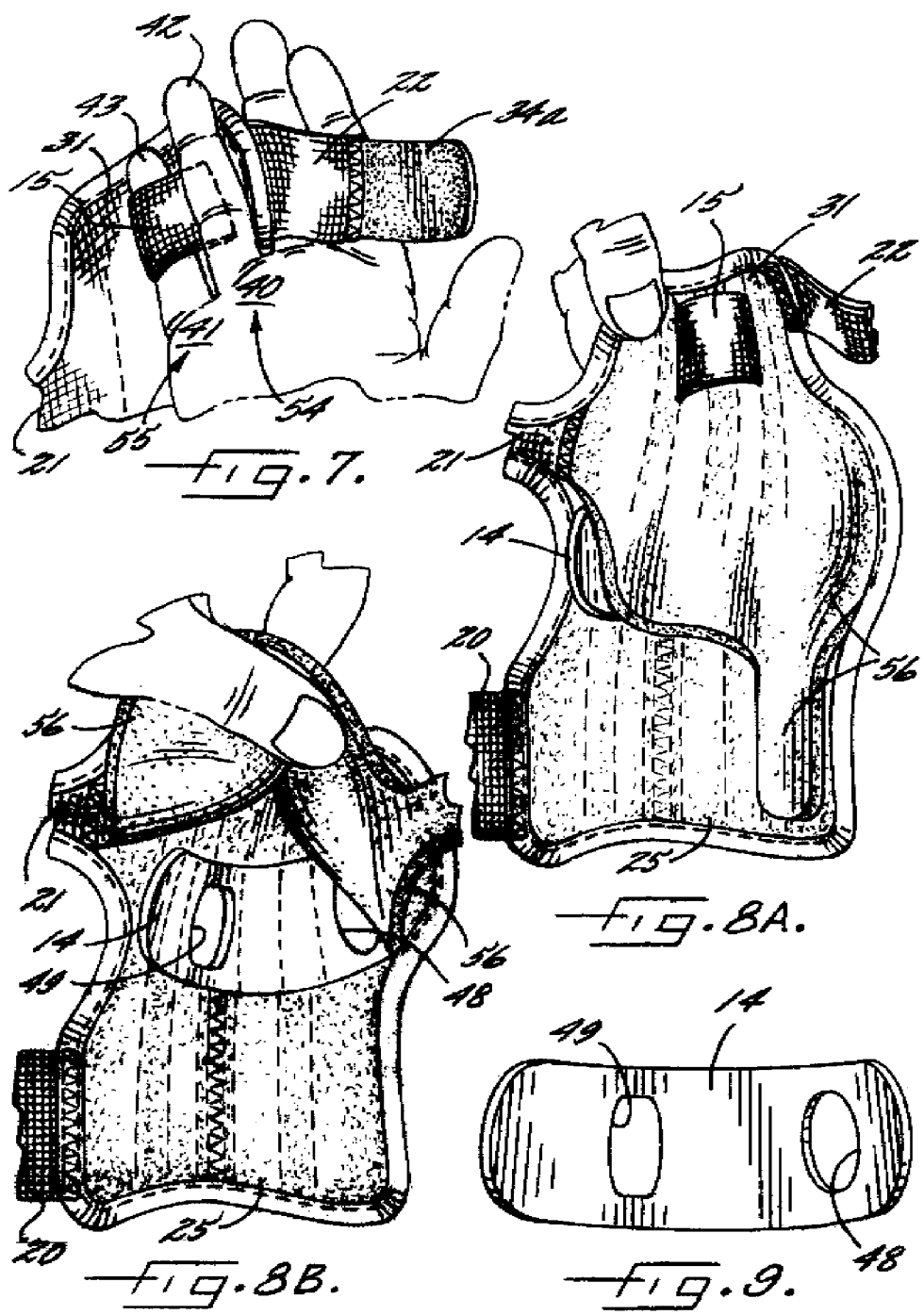

HAND BRACE FOR IMMOBILIZING AND ADJUSTABLY POSITIONING ONE OR MORE DIGITS

BACKGROUND OF THE INVENTION

The invention relates to a hand brace for immobilizing and adjustably positioning one or more digits of the hand, and more specifically, to a brace having a flexible sheet member, at least one adjustable stabilizing member that is sufficiently rigid to maintain joints at a desired angle of flexion, and a semi-rigid member positioned against the flexible sheet member for protecting and supporting joints of the hand. Advantageously the invention immobilizes the hand such that the fourth and fifth metacarpophalangeal joints of the hand are positioned at a desired angle of flexion and the fourth and fifth interphalangeal joints of the hand are positioned at full extension.

As known by boxers or participants in combat athletics, a "boxer's fracture" commonly refers to a fracture at the neck of the fifth metacarpal bone (i.e., the little finger or pinky finger) which is the most lateral metacarpal of a human hand. Except in unique instances, a human hand is comprised of four fingers and a thumb. Beginning with the closest finger to the thumb (i.e., first digit), each finger is colloquially referred to as follows: index finger or forefinger (i.e., second digit), middle finger (i.e., third digit), ring finger (i.e., fourth digit), and little finger (i.e., fifth digit).

The hand is also comprised of bones and joints that form the fingers, thumb, and palm. Beginning at the wrist, the bones of the hand include carpals, metacarpals, proximal phalanges, intermediate phalanges, and distal phalanges. The joints of the hand include, among others, the metacarpophalangeal and interphalangeal joints.

The metacarpophalangeal joints are located between the rounded heads of the metacarpals and the shallow cavities on the proximal ends of the first or proximal phalanges of the fingers with the exception of the thumb.

The interphalangeal joints are hinge-joints of the phalanges of the hand. Absent the thumb, each finger of the human hand has two sets of interphalangeal joints, namely, the proximal interphalangeal joints and the distal interphalangeal joints. The proximal interphalangeal joints are located between the first (or proximal) phalanges and second (or intermediate) phalanges. The distal interphalangeal joints are located between the second phalange and third (distal) phalange.

A boxer's fracture is usually caused by the impact of a clenched first with a skull or a hard, immovable object, such as a wall or a door. During a boxer's swing, for example, the knuckle or metacarpophalangeal joint of the little finger (i.e., fifth metacarpal) tends to lead the rest of the knuckles in a hard punch. Upon impact, the knuckle compresses and snaps or fractures the distal end of the metacarpal.

Such fractures are often angulated, and if severely so, the fracture requires pins and realignment as well as a splint. Total healing time typically does not exceed more than 12 weeks. Soft casts or splints are preferred over hard casts because the splint or brace can be removed for brief periods of time to allow for bathing and to avoid skin irritation. The typical rehabilitation period is approximately four months with adequate therapy.

The preferred positioning of the hand in a splint or brace is referred as the "intrinsic plus position." In this position, the hand can be immobilized for long periods of time and joint stiffness is reduced as compared to alternative positioning of the digits. In the intrinsic plus position, the metacarpophalangeal joints are flexed at 60 to 70 degrees and the interphalangeal joints are fully extended. The wrist is positioned in extension at 10 degrees less than maximal.

In the intrinsic plus position, the metacarpophalangeal joints are in flexion and the interphalangeal joints are in full extension. "Flexion" of the fingers and joints refers to a bending movement that decreases the angle between two parts of, for example, the finger. "Extension" of the fingers and joints, the opposite of flexion, refers to a straightening movement that increases the angle between the body parts.

It is understood that flexion of the fingers promotes recovery of the metacarpophalangeal joints, and extension of the fingers promotes recovery of the interphalangeal joints, based on differences in the shape of the metacarpal head, volar plate, and collateral ligament anatomy of the hand and wrist. The metacarpal head is uniquely shaped in that it is ovoid in the sagittal plane, and widens from the dorsal to the volar or palmar dimension. The collateral ligaments are eccentrically mounted dorsal to the axis of rotation of the metacarpophalangeal joint. This anatomy causes variable degrees of tightness on the collateral ligaments based on the position of the joint by a cam-like effect. When the joint is in extension, the collateral ligaments are lax. When the joint is in flexion, the collateral ligaments span a greater distance and are tight.

In addition, the metacarpophalangeal joint is also curved in two planes to permit abduction (i.e., a motion that pulls the fingers away from the midline of the body as in spreading the digits apart and away from the centerline of the hand), adduction (i.e., a motion that pulls the fingers towards the midline of the body as in closing the digits together), and rotation, as well as flexion and extension in an abbreviated ball-and-socket configuration. In flexion, bone surface area contact is greater than in extension, thereby producing a more stable joint.

Accordingly, the hands, and specifically the metacarpophalangeal joints are particularly vulnerable to fractures. Athletes experiencing a boxer's fracture often utilize some form of hand and wrist support during recovery. Many athletes rely upon a splint and taping to provide support during recovery. Although known splints and taping stabilize the metacarpophalangeal joints a number of drawbacks exist. For example, known splints may restrict all motion of the hand and fingers, both desirable and undesirable. Further, known splints fail to simultaneously provide sufficient support of the hand and fingers in the intrinsic plus position wherein metacarpophalangeal joints are flexed between about 60 to 70 degrees, and the interphalangeal joints may be fully extended, while providing support and protection of one or more metacarpals. The restrictive characteristics of known splints thus hinder proper recovery of boxer fractures.

SUMMARY OF THE INVENTION

The inventive hand brace of the present invention simultaneously provides sufficient support of the hand and fingers in the intrinsic plus position wherein the fourth and fifth metacarpophalangeal joints are flexed at 60 to 70 degrees and the fourth and fifth interphalangeal joints are fully extended, while providing support and protection of the fourth and fifth metacarpals.

The hand brace comprises in one embodiment a flexible sheet member, at least one adjustable stabilizing member fixed to the flexible sheet member, a semi-rigid member positioned against the flexible sheet member, a flexible panel spanning sections of the sheet member for receiving a digit, a positioning strap, an adjustable closure strap, and a tensioning strap. As configured the hand brace immobilizes the hand such that the fourth and fifth metacarpophalangeal joints of the hand are positioned at a desired angle of flexion and the fourth and fifth interphalangeal joints are positioned at full extension. This position of the joints and fingers promotes recovery of a boxer's fracture.

The flexible sheet member wraps around a portion of the hand and wrist, and includes a dorsal section, a palmar section, a proximal section, an intermediate section, a distal section, an interior surface, and an exterior surface. At least one stabilizing member is fixed to the flexible sheet member and extends along a portion of the length of the sheet member. The stabilizing member is manually adjustable yet sufficiently rigid to resist movement of the proximal and distal sections of the sheet member relative to one another.

The semi-rigid member is substantially L-shaped or C-shaped, and positioned against the intermediate section of the flexible sheet member. In particular, the semi-rigid member spans across the intermediate section of the sheet member and shapes the dorsal and palmar sections of the sheet member to conform to the hand upon application.

A flexible panel is connected to the dorsal and palmar sections of the sheet member at a distal end thereof and forms an area for receiving one or more digits (e.g., ring and pinky finger).

The invention also includes a number of straps extending from the brace for adjustably securing the hand brace on the wrist and fingers. A positioning strap releasably connects portions of the proximal section of the sheet member. An adjustable closure strap releasably connects portions of the intermediate section of the sheet member. A tensioning strap carried by the sheet member releasably connects portions of the distal section of the sheet member.

The invention further includes a receiving member fixed to the dorsal section of the sheet member opposite the palmar section. The adjustable closure strap promotes adjustability by passing through the receiving member and removably attaching to the palmar section of the sheet member.

The invention also includes padding fixed to interior surfaces of the sheet member for engaging the hand and promoting comfort during wear.

BRIEF DESCRIPTION OF THE DRAWINGS

The foregoing and other objects and advantages of the invention and the manner in which the same are accomplished will become clearer based on the following detailed description taken in conjunction with the accompanying drawings in which:

FIG. 1 is a perspective view of one embodiment of the hand brace of the invention;

FIG. 2 is a perspective view of one embodiment of the hand brace of FIG. 1;

FIG. 3 is an enlarged perspective view of one embodiment of the hand brace of FIG. 1 depicting a receiving member and portions of an adjustable closure strap extending there through;

FIG. 4 is a top plan view of one embodiment of the hand brace of FIG. 1 depicting stabilizing members and an exterior surface of the hand brace;

FIG. 5 is a top plan view of one embodiment of the hand brace of FIG. 1 depicting an interior surface of the hand brace;

FIG. 6 is a perspective view of a stabilizing member of one embodiment of the hand brace of FIG. 1 depicting an angle of flexion;

FIG. 7 is an enlarged perspective view of a distal section of one embodiment of the hand brace of FIG. 1;

FIG. 8A is a partial perspective view of the interior surface of one embodiment of the hand brace of FIG. 1;

FIG. 8B is an enlarged perspective view of the interior surface, padding, and a semi-rigid member of one embodiment of the hand brace of FIG. 1; and FIG. 9 is a perspective view of the semi-rigid member of one embodiment of the hand brace of FIG. 1.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

An overall view of an embodiment of a hand brace 10 of the present invention is set forth at 10 in the perspective view of FIG. 1. The hand brace 10 is configured for wear on the right or left hand. Therefore FIG. 1 illustrates the brace 10 as it appears when worn on a right hand. When worn on a left hand, the brace 10 would be a mirror-image version of the one illustrated in FIG. 1.

Advantageously, the hand brace 10 immobilizes the hand such that fourth and fifth metacarpophalangeal joints 40, 41 of the hand are positioned at a desired angle of flexion (e.g., 60 to 70 degrees), and the fourth and fifth interphalangeal joints 42, 43 of the hand are positioned at a desired angle of extension (i.e., in the intrinsic plus position), while providing support and protection of the fourth and fifth metacarpals 54, 55 against impact.

Referring to the exemplary embodiment of the hand brace 10 depicted in FIG. 4, the configuration of the elements of the apparatus will be summarized as follows, with alternative embodiments discussed thereafter. The brace 10 for immobilizing and positioning one or more digits may include a flexible sheet member 11, at least one adjustable stabilizing member 12, 13 fixed to the flexible sheet member 11, a semi-rigid member 14 positioned against the flexible sheet member 11, a flexible panel 15 spanning sections of the sheet member 11 for receiving a digit, a positioning strap 20, an adjustable closure strap 21, and a tensioning strap 22.

As used herein, the phrase "positioned against" or "extend against" means that one element may be fixed (i.e., secured) or releasably attached to another element. Thus, the phrase "positioned against" will not exclude the option of a first element being secured or releasably attached to a second element. Accordingly, a first element may be positioned against a second element by sewing, hook and loop fasteners, or a loop that is fixed to the second element for receiving or engaging the first element. It will also be appreciated that the terms "fixed" and "secured" may include sewn, made integral with, adhered with adhesive, or bonded with heat.

In one embodiment, and referring to FIGS. 4 and 5, the flexible sheet member 11 is comprised of a dorsal section 23 for application against the dorsal portion of a hand, a palmar section 24 for application against the palm of the hand, a proximal section 25 for receiving a wrist, an intermediate section 30, and a distal section 31 for receiving a fourth and fifth digit (i.e., ring finger and pinky finger). It will be understood that the terms "section" and "portion" refer to various areas of the brace 10. It will be further understood that the term "dorsal" refers to the back of the brace 10 or hand, and the term "palmar" refers to the anterior of the brace 10 or hand. The term "proximal" refers to the part of the brace 10 or hand that is closest to, or attached to, the body, and the term "distal" refers to the part of the brace 10 or hand furthest from the body. When referring the brace 10, the term "intermediate" refers to the section of the hand brace 10 that is between the proximal and distal sections 31 of the brace.

The sheet member 11 defines an interior surface 32 and an exterior surface 33. With reference to the orientation of the brace 10 in FIGS. 1 and 2, it will be understood that the terms "interior surface" and "exterior surface" may be referred to as "inside surface" and "outside surface." Stated differently, as used herein the term interior surface 32 implies the side of the sheet member 11 closest to the hand of the wearer. Thus, it will be understood that the term exterior surface 33 implies the side of the sheet member 11 opposite the interior surface 32 (i.e., the side farthest from the hand of the wearer).

The exterior surface 33 of the sheet member 11 may include fasteners 34 for removably attaching portions of the positioning strap 20, adjustable closure strap 21, and tensioning strap 22 having hook fasteners 34a to portions of the exterior surface 33 of the flexible sheet member 11. In one embodiment, portions of the exterior surface 33 of the sheet member 11 and portions of the straps (e.g., free end portions) may include corresponding hook and loop fasteners 34a, 34b.

The sheet member 11 may be fabricated from one or more layers of a pliable fabric material. Advantageously, the pliable fabric material will conform to a hand and wrist, yet minimize any stretching familiar to elastic material. As used herein, it will be understood that the term "elastic" refers to material that is capable of being easily stretched or expanded, and resuming its former shape. Stated differently, the term elastic implies the property of resisting deformation by stretching. In a related aspect, it will be understood that the term "inelastic" refers to material that resists stretching and elongation.

The sheet member 11 is desirably seamed to form a configuration for covering at least a portion of a wrist and hand. In one embodiment of the brace 10, straps are secured to (e.g., stitched) edge portions of a single sheet member 11 formed of felt-like pliable material. It will be understood that any number of sheet members may be incorporated into the hand brace 10.

Referring to FIGS. 4 and 6, the invention provides at least one stabilizing member 12, 13 that is fixed to the flexible sheet member 11. The at least one stabilizing member 12, 13 extends along the length of at least a portion of the sheet member 11 and against the semi-rigid member 14. The at least one stabilizing member 12, 13 is adjustable yet sufficiently rigid to resist movement of the proximal and distal sections 31 of the sheet member 11 relative to one another. The at least one stabilizing member 12, 13 may be formed from metal, alloy, or any number of materials providing sufficient rigidity to resist movement and retain a desired shape, yet maintain adequate adjustability for wear on the wrist and hand (e.g., aluminum). Adjustment provided by, for example, an aluminum stabilizing member, is accomplished without additional mechanical devices (e.g., a locking slide) or heat requirements (e.g., heating and molding the body member).

In one embodiment, the invention provides first and second stabilizing members 12, 13 that extend substantially the length of the dorsal and palmar sections 23, 24 of the sheet member 11 (see FIG. 4). In this embodiment, both the first and second stabilizing members 12, 13 are manually adjustable yet sufficiently rigid to maintain a fourth and fifth metacarpophalangeal joint 40, 41 of the hand at a desired angle of flexion α (see FIG. 6). A preferred angle of flexion α for promoting recovery of a boxer's fracture may be between about 45 and 90 degrees, and more preferably between about 60 and 70 degrees. It will be understood, however, that the degree of flexion of the fourth and fifth metacarpophalangeal joints 40, 41 may be from about 0 to 90 degrees of flexion. The desired degree of extension of the fourth and fifth interphalangeal joints 42, 43 may be between about 25 degrees to full extension.

Upon application of the hand brace 10, the first and second stabilizing members 12, 13 oppose one another and extend against opposing portions of the semi-rigid member 14. Stated differently, the first and second stabilizing members 12, 13 extend along the dorsal and palmar sections of the hand. In one embodiment, the first and second stabilizing members 12, 13 are positioned against the exterior surface 33 of the flexible sheet member 11. The first and second stabilizing members 12, 13 may be fixed to the exterior surface 33 of the brace 10 with strips 44 of inelastic fabric material stitched to the sheet member 11 to secure the stabilizing members 12, 13 thereto. In this particular embodiment of the invention, the substantially inelastic material is a knitted nylon fabric, as such fabrics have been found to be light weight, while providing a high degree of strength and durability. Fasteners 34 on the exterior surface 33 of the sheet member 11 may include fastener loops 34b on the strips 44 that secure the stabilizing members 12, 13 to the brace 10.

As illustrated in FIG. 5, the semi-rigid member 14 is positioned against and spans across the intermediate section 30 of the flexible sheet member 11 and shapes the dorsal and palmar sections 23, 24 of the sheet member 11. Stated differently, the semi-rigid member 14 promotes curvature of the sheet member 11 about the hand. The semi-rigid member 14 may be formed from any number of inelastic materials (e.g. polymeric material) that provide a semi-rigid characteristic to the member.

As illustrated in one embodiment, the semi-rigid member 14 is oblong and substantially L-shaped. The semi-rigid member 14 may also be substantially rectangular, substantially triangular, substantially polygonal, substantially circular, or any number of shapes sufficient to promote curvature of the flexible sheet member 11 and protect one or more metacarpophalangeal joints of the hand. It will be understood that the terms "substantially rectangular", "substantially triangular", "substantially polygonal" and "substantially circular" are meant to succinctly describe a simple geometric shape approximating a rectangle, triangle, polygon, or circle, respectively.

The semi-rigid member 14 extends across the intermediate section 30 of the sheet member 11 to protect and support the fourth and fifth metacarpophalangeal joints 40, 41 of the hand (see FIGS. 1, 2, and 8B). The semi-rigid member 14 may define at least one opening 48 for relieving pressure on at least one joint of the hand, for example, a second metacarpophalangeal joint of the hand. The semi-rigid member 14 may also define another opening 49 in an intermediate portion thereof to promote curvature of the semi-rigid member 14 about one or more metacarpals of the hand, and more particularly about the fourth and fifth metacarpophalangeal joints 40, 41.

The semi-rigid member 14 may be positioned against the interior surface 32 of the flexible sheet member 11. It will be understood however that the semi-rigid member 14 may also be positioned against the exterior surface 33 of the hand brace 10.

As depicted in FIGS. 7 and 8A, the flexible panel 15 is connected to dorsal and palmar sections 23, 24 of the interior surface 32 of the flexible sheet member 11 at a distal end of the brace 10. The flexible panel 15 is designed to receive a digit, for example, a fifth digit or pinky finger. By doing so, the flexible panel 15 provides a slight separation between the fourth and fifth digit to allow air to circulate there between. The flexible panel 15 contributes to the isolation and immobilization of the fourth and fifth fingers and metacarpophalangeal joints 40, 41 as illustrated in FIGS. 1, 2, and 7. Stated differently, the flexible panel 15 spans the dorsal and palmar sections 23, 24 of said flexible sheet member 11 and forms an area for receiving at least a portion of the fifth digit.

Referring to FIGS. 1, 5, and 6, the positioning strap 20 is carried by the flexible sheet member 11 and releasably connects portions of the proximal section 25 of the sheet member 11 upon application of the brace 10 to the wrist and hand. The positioning strap 20 extends from the proximal section 25 of the sheet member 11 and flexibly secures the brace 10 against the wrist. More particularly, the positioning strap 20 extends from one side of the proximal section 25 of the flexible sheet member 11. In one embodiment, the positioning strap 20 and the tensioning strap 22 are elastic and promote adjustability of the hand brace 10 to the wrist and hand.

As shown in FIGS. 1 and 5, the adjustable closure strap 21 is also carried by the flexible sheet member 11 and releasably connects portions of the intermediate section 30 of the sheet member 11. More specifically, the adjustable closure strap 21 extends from the intermediate section 30 of the sheet member 11 and has a free end that extends through a receiving member 50 fixed to the flexible sheet member 11. The free end of the adjustable closure strap 21 removably attaches to the intermediate section 30 of the sheet member 11 upon application. Stated differently, the adjustable closure strap 21 extends from an edge of the palmar section 24 of the flexible sheet member 11, and the free end extends through the receiving member 50 and removably attaches to the palmar section 24 of the sheet member 11. Advantageously, the closure strap 21 adjustably secures the semi-rigid member 14 against the fourth and fifth metacarpals 54, 55 of the hand to thereby protect and support the fourth and fifth metacarpals 54, 55 from impact.

The receiving member 50 is fixed to the dorsal section 23 of the flexible sheet member 11 (see FIGS. 2 and 3). Referring to FIG. 4, the receiving member 50 is positioned opposite an end of the adjustable closure strap 21 that is fixed to the palmar section 24 of the sheet member 11. In one embodiment, the adjustable closure strap 21 is inelastic yet promotes adjustability by passing across the palm, through the receiving member 50, back across the palm, and removably attaching to the palmar section 24 of the flexible sheet member 11. This configuration promotes secure fitment of the brace 10 to a hand and accounts for varying stages of swelling during the healing process of the hand.

The tensioning strap 22 is carried by the flexible sheet member 11 and releasably connects portions of the distal section 31 of the sheet member 11. In particular, the tensioning strap 22 extends from the distal section 31 of the flexible sheet member 11 and isolates and immobilizes a fourth and fifth digit of the hand at a desired angle of flexion α. Stated differently, the tensioning strap 22 extends from one side of the distal section 31 of the flexible sheet member 11 for isolating and immobilizing the fourth and fifth digits.

In one embodiment, the positioning strap 20, adjustable closure strap 21, and tensioning strap 22 have free ends with fastener hooks 34a for removably attaching the straps to the flexible sheet member 11. As set forth above, portions of the exterior surface 33 of the sheet member 11 and portions of the straps may include corresponding hook and loop fasteners 34a, 34b.

The invention may also include padding 56 secured to the interior surface 32 of flexible sheet member 11 over the semi-rigid member 14. As depicted in FIGS. 8A and 8B, the padding 56 may cover the semi-rigid member 14 and engage portions of the hand. The padding 56 provides a layer between the semi-rigid member 14 and the user's hand. It will also be understood that as used herein, the concept of an element (e.g., padding 56) being "between" two other elements does not necessarily imply that the three elements are contiguous (i.e., in intimate contact). Rather, as used herein, the concept of one element being between two other elements is meant to describe the relative positions of the elements within the brace 10 structure, respectively. The padding 56 may be a sheet or sheets of foam material. It will be understood that the padding 56 may be continuous or patterned.

As configured, the novel configuration of the hand brace 10 described above immobilizes the hand such that fourth and fifth metacarpophalangeal joints 40, 41 are positioned at a desired angle of flexion, and the fourth and fifth interphalangeal joints 42, 43 are positioned at a desired angle of extension. In particular, the distal section 31 of the brace 10, tensioning strap 22, and adjustable stabilizing members 12, 13 immobilize the fourth and fifth metacarpophalangeal joints 40, 41 at a desired angle of flexion and the fourth and fifth interphalangeal joints 42, 43 at full extension. Moreover the semi-rigid member 14 protects and supports the fourth and fifth metacarpals 54, 55 without restricting flexion of the metacarpophalangeal joints.

In operation, the stabilizing members 12, 13 are manually adjusted to reflect a desired angle of flexion α of the fourth and fifth digits. The brace 10 is then placed against the individual's wrist and hand, and the fifth digit is placed under the flexible panel 15. Once the brace 10 is stationary against the wrist and hand, the positioning strap 20 is wrapped about the wrist and the free end of the positioning strap 20 is releasably attached to a fastener 34 on the exterior surface 33 of the sheet member 11. As noted above, the free end of the positioning strap 20 and the exterior surface 33 of the sheet member 11 may include corresponding hook and loop fasteners 34a, 34b.

In an exemplary description wherein the closure strap 21 has not passed through the receiving member 50, the closure strap 21 is next drawn between the first and second digits (i.e., thumb and index finger), against the second metacarpophalangeal joint, and the free end of the strap is passed through the receiving member 50. Thereafter, the free end of the closure strap 21 is drawn back between the first and second digits, and releasably attached to a fastener 34 on the exterior surface 33 of the sheet member 11. As discussed above, the free end of the closure strap 21 and the exterior surface 33 of the sheet member 11 may include corresponding hook and loop fasteners 34a, 34b.

Next the tensioning strap 22 is drawn between the third and fourth digits and across the distal and intermediate phalanges thereof. An appropriate amount of tension is applied to the tensioning strap 22 depending upon the degree of swelling of the fractured fifth metacarpal. The free end of the tensioning is releasably attached to a fastener 34 on the exterior surface 33 of the sheet member 11. As previously stated, the free end of the tensioning strap 22 and the exterior surface 33 of the sheet member 11 may include corresponding hook and loop fasteners 34a, 34b.

Alternatively, the tensioning strap 22 may be releasably attached to the sheet member 11 prior to the closure strap 21.

Advantageously, once the free end of the closure strap 21 is passed through the receiving member 50, the closure strap 21 is prevented from sliding out of the member when applying or removing the brace 10.

In the drawings and specification, there have been disclosed typical embodiments on the invention and, although specific terms have been employed, they have been used in a generic and descriptive sense only and not for purposes of limitation, the scope of the invention being set forth in the following claims.

That which is claimed is:

1. A hand brace for immobilizing and positioning one or more digits, said hand brace comprising:
    a flexible sheet member having a dorsal section, a palmar section, a proximal section, an intermediate section, a distal section, an interior surface, and an exterior surface;
    at least one stabilizing member fixed to said flexible sheet member and extending the length of at least a portion thereof, said stabilizing member being adjustable yet sufficiently rigid to resist movement of said proximal and distal sections of said flexible sheet member relative to one another;
    a semi-rigid member positioned against and spanning across said intermediate section of said flexible sheet member for shaping said dorsal and palmar sections of said flexible sheet member; and
    a tensioning strap carried by said flexible sheet member for releasably connecting portions of said distal section of said flexible sheet member;
    wherein said hand brace immobilizes the hand such that fourth and fifth metacarpophalangeal joints of the hand are positioned at a desired angle of flexion, and fourth and fifth interphalangeal joints of the hand are positioned at a desired angle of extension.

2. A hand brace according to claim 1 wherein said at least one stabilizing member extends substantially against said semi-rigid member.

3. A hand brace according to claim 1 wherein said semi-rigid member defines at least one opening for promoting curvature of said semi-rigid member.

4. A hand brace according to claim 1 wherein said semi-rigid member defines at least one opening for relieving pressure on at least one joint of the hand.

5. A hand brace according to claim 1 wherein said desired angle of flexion is between about 45 and 90 degrees.

6. A hand brace according to claim 1 further comprising a flexible panel connected to said dorsal and palmar sections of said flexible sheet member at a distal end thereof for receiving a digit.

7. A hand brace according to claim 1 further comprising a positioning strap carried by said flexible sheet member for releasably connecting portions of said proximal section of said flexible sheet member.

8. A hand brace according to claim 7 wherein said positioning strap and said tensioning strap are elastic and promote adjustability of said hand brace.

9. A hand brace according to claim 1 further comprising an adjustable closure strap carried by said flexible sheet member for releasably connecting portions of said intermediate section of said flexible sheet member.

10. A hand brace according to claim 9 further comprising:
    a receiving member fixed to said dorsal section of said flexible sheet member opposite an end of said adjustable closure strap fixed to said palmar section of said flexible sheet member;
    wherein said adjustable closure strap is inelastic yet promotes adjustability by passing through said receiving member and removably attaching to said palmar section of said flexible sheet member.

11. A hand brace according to claim 1 further comprising fasteners positioned against said exterior surface of said flexible sheet member for removably attaching at least one strap to at least a portion of said exterior surface of said flexible sheet member.

12. A hand brace according to claim 1 further comprising padding fixed to said interior surface of said flexible sheet member.

13. A hand brace for immobilizing and positioning one or more digits, said brace comprising:
    a flexible sheet member having a dorsal section, a palmar section, a proximal section for receiving a wrist, an intermediate section, a distal section for receiving a fourth and fifth digit, an interior surface, and an exterior surface;
    a first and second stabilizing member extending substantially the length of said dorsal and palmar sections of said flexible sheet member, said first and second stabilizing members being manually adjustable yet sufficiently rigid to maintain a fourth and fifth metacarpophalangeal joint of the hand at a desired angle of flexion;
    a semi-rigid member positioned against and extending across said intermediate section of said flexible sheet member for protecting and supporting the fourth and fifth metacarpophalangeal joints of the hand and for shaping said dorsal and palmar sections of said flexible sheet member, said semi-rigid member defining at least one opening for relieving pressure on a second metacarpophalangeal joint of the hand;
    a flexible panel connected to said dorsal and palmar sections of said flexible sheet member at a distal end thereof for receiving a fifth digit of a hand;
    a positioning strap extending from said proximal section of said flexible sheet member for flexibly securing said brace against a wrist;
    an adjustable closure strap extending from said intermediate section of said flexible sheet member, said adjustable closure strap having a free end that extends through a receiving member fixed to said flexible sheet member and removably attaches to said intermediate section of said flexible sheet member; and
    a tensioning strap extending from said distal section of said flexible sheet member for isolating and immobilizing a fourth and fifth digit at a desired angle of flexion;
    wherein said hand brace immobilizes the hand such that the fourth and fifth metacarpophalangeal joints of the hand are positioned at a desired angle of flexion and fourth and fifth interphalangeal joints of the hand are positioned at full extension.

14. A hand brace according to claim 13 wherein said first and second stabilizing members oppose one another upon application of said brace to the hand and extend against opposing portions of said semi-rigid member.

15. A hand brace according to claim 13, wherein said first and second stabilizing members are positioned against said exterior surface of said flexible sheet member.

16. A hand brace according to claim 13 wherein said semi-rigid member defines at least another opening that promotes curvature of said semi-rigid member about one or more metacarpals of the hand.

17. A hand brace according to claim 13 wherein said semi-rigid member is positioned against said interior surface of said flexible sheet member.

18. A hand brace according to claim 13 wherein said adjustable closure strap adjustably secures said semi-rigid member substantially against fourth and fifth metacarpals of the hand to thereby protect and support the fourth and fifth metacarpals.

19. A hand brace according to claim 13 wherein said positioning strap, said adjustable closure strap, and said tensioning strap having free ends with fasteners for removably attaching said straps to said flexible sheet member.

20. A hand brace according to claim 13 wherein said desired angle of flexion is between about 45 and 90 degrees.

21. A hand brace according to claim 13 further comprising padding for engaging portions of the hand.

22. A hand brace for immobilizing and positioning one or more digits, said brace comprising:
- a flexible sheet member having a dorsal section, a palmar section, a proximal section for receiving a wrist, an intermediate section, a distal section for receiving a fourth and fifth digit, an interior surface, and an exterior surface;
- a first and second stabilizing member extending the length of said dorsal and palmar sections of said flexible sheet member, said first and second stabilizing members being manually adjustable yet sufficiently rigid to maintain a fourth and fifth metacarpophalangeal joint of the hand at a desired angle of flexion;
- a semi-rigid member positioned against and spanning across an intermediate section of said flexible sheet member for protecting and supporting the fourth and fifth metacarpophalangeal joints of the hand and for shaping said dorsal and palmar sections of said flexible sheet member, said semi-rigid member defining a first opening for relieving pressure on a second metacarpophalangeal joint of the hand and a second opening for promoting curvature about one or more metacarpals of the hand;
- a flexible panel spanning said dorsal and palmar sections of said flexible sheet member at a distal end thereof for receiving a fifth digit of a hand;
- a receiving member fixed to said dorsal section of said flexible sheet member;
- a positioning strap extending from one side of said proximal section of said flexible sheet member for flexibly securing said brace against a wrist;
- an adjustable closure strap extending from an edge of said palmar section of said flexible sheet member, said adjustable closure strap having a free end that extends through said receiving member and removably attaches to said palmar section of said flexible sheet member; and
- a tensioning strap extending from one side of said distal section of said flexible sheet member for isolating and immobilizing portions of a fourth and fifth digit at a desired angle of flexion and extension.

23. A hand brace according to claim 22 wherein said hand brace immobilizes the hand such that the fourth and fifth metacarpophalangeal joints of the hand are positioned at a desired angle of flexion and fourth and fifth interphalangeal joints of the hand are positioned at a desired angle of extension.

* * * * *

UNITED STATES PATENT AND TRADEMARK OFFICE
CERTIFICATE OF CORRECTION

| | |
|---|---|
| PATENT NO. | : 8,246,560 B2 |
| APPLICATION NO. | : 12/542959 |
| DATED | : August 21, 2012 |
| INVENTOR(S) | : Gaylord et al. |

It is certified that error appears in the above-identified patent and that said Letters Patent is hereby corrected as shown below:

Column 1, line 49 reads "clenched ~~first~~ with a skull or a hard, immovable object, such" and should read "clenched <u>fist</u> with a skull or a hard, immovable object, such"

Signed and Sealed this
Thirtieth Day of October, 2012

David J. Kappos
*Director of the United States Patent and Trademark Office*